US00PP22725P2

(12) United States Plant Patent
Gossett

(10) Patent No.: US PP22,725 P2
(45) Date of Patent: May 8, 2012

(54) ***HOSTA* PLANT NAMED 'PURPLE HEART'**

(50) Latin Name: *Hosta hybrida*
Varietal Denomination: Purple Heart

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 2 days.

(21) Appl. No.: 12/927,268

(22) Filed: Nov. 10, 2010

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt
(74) *Attorney, Agent, or Firm* — Klarquist Sparkman, LLP

(57) ABSTRACT

A new and distinct *Hosta* plant characterized by very dark maroon petioles with maroon leaf bases, thick, glossy, dark green leaves, camptodrome venation, a vigorous, clumping habit, on a medium size plant.

1 Drawing Sheet

Botanical denomination: *Hosta hybrida.*
Variety designation: 'Purple Heart'.

BACKGROUND OF THE INVENTION

The present invention relates to a new and distinct cultivar of *Hosta*, botanically known as a *Hosta hybrida*, and hereinafter will be referred to by its cultivar name 'Purple Heart'. *Hosta* is in the family Hostaceae. The plant is the culmination of a breeding program for red petiole and leaf base *Hosta*. It was bred in Canby, Oreg. using unpatented proprietary parents. The exact parents are unknown.

Compared to *Hosta* 'Invincible' (an unpatented plant), *Hosta* 'Purple Heart' has a similar leaf color and texture. The new variety has a dark leaf base and a darker petiole.

Compared to *Hosta* 'Little Red Rooster' (an unpatented plant), *Hosta* 'Purple Heart' is a larger plant with deeper green foliage and a dark leaf base that continues further up the leaf.

Compared to *Hosta* 'Red October' (an unpatented plant), *Hosta* 'Purple Heart' has a larger habit and a deeper color in the leaf base.

SUMMARY OF THE INVENTION

This new cultivar is unique in the combination of:

1. very dark maroon petioles with maroon leaf bases,
2. thick, glossy, dark green leaves,
3. camptodrome venation,
4. a vigorous clumping habit,
5. and a medium size plant.

This new cultivar has been reproduced only by asexual propagation (division and tissue culture). Each of the progeny exhibits identical characteristics to the new cultivar. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a two-year-old plant in a 4 inch pot in July in Canby, Oreg.

FIG. 2 shows flower stalk in late September.

DETAILED PLANT DESCRIPTION

The following is a detailed description of the new *Hosta* cultivar based on observations of one-and-a-half-year-old specimens growing in shade in the garden in mid-September in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 4 to 9.
*Size.*—Grows to 54 cm wide and 31 cm tall from the top of the soil to the top of the foliage.
*Form.*—Clumping.
*Number of crowns per plant.*—About 6.
*Number of leaves per crown.*—6 to 12.

Leaf:

*Type.*—Simple.
*Shape.*—Ovate.
*Arrangement.*—Basal rosette.
*Blade size.*—Grows to 18.5 cm long and 11.7 cm wide.
*Margins.*—Entire.
*Apex.*—Caudate.
*Base.*—Truncate.
*Petiole.*—13 cm to 17 cm long and 7 mm to 9 mm wide, clasping, glabrous, cupped, inner and outer surface heavily spotted Greyed Purple N187A.
*Texture.*—Leathery.
*Surface texture.*—Glabrous on both surfaces, glossy on bottom surface.
*Venation.*—Average of 6 pairs of veins, camptodrome pattern, impressed on upper surface and raised on lower surface.
*Color.*—Topside Green 138A, lightening to Green 137A with base and up the main vein heavily spotted Greyed Purple N187A; bottom side Yellow Green 146B with side veins and main vein Greyed Purple N187A.

Inflorescence:

*Type*.—Self cleaning; terminal raceme.

*Number of flowers per raceme*.—About 30.

*Peduncle description*.—Grows to 38 cm long and 6 mm wide, glabrous, Greyed Purple N186C on bottom half to Greyed Purple N186A on top half.

*Pedicel description*.—Grows to 3 cm long and 1 mm wide, glabrous, Violet 83A.

*Floral bracts*.—One at the base of each pedicel, at a 50 degree angle, grows to 3.5 cm long and 18 mm wide, becoming progressively smaller going up the peduncle, ovate, margin entire, tip acute, glabrous on both sides, clasping, cupping upward; top and bottom side Purple N187A on top half to Purple 79A at the base.

*Bloom time*.—August to October in Canby, Oreg.

*Lastingness of inflorescence*.—6 to 8 weeks.

Flower bud:

*Size*.—35 mm long and 8 mm wide.

*Shape*.—Oblong, narrowed on bottom ⅓.

*Surface texture*.—Glabrous.

*Color*.—Violet 86A to Violet 86C.

Flower:

*Type*.—Perfect.

*Shape*.—Campanulate, drooping slightly.

*Size*.—Average 6 cm long and 2.3 cm wide.

*Surface texture*.—Glabrous inside and out.

*Corolla description*.—6 overlapping tepals, lobes overlapping, tube 2 cm long and 2.5 mm wide; tepal lobes ovate, margins entire, tip acute, 25 mm long and 10 mm wide; tepal outside and inside color closest to Violet 85A, tube closest to Violet 85A.

*Pistil description*.—62 mm long, ovary 8 cm long and 2 mm wide, Greyed Purple N186A, style 5.5 cm long, Greyed Purple N187B on bottom half to Green White 157B on top half, stigma Greyed Purple N186A.

*Stamen*.—6, filaments 5 cm long, Green White 157C, anthers 3 mm long and 1 mm wide, Grey Brown N199B, pollen Yellow Orange 14B.

*Fragrance*.—None.

Fruit and seed: None produced.

Pest and diseases: Snail and slugs are the main problems on *Hosta*. This new cultivar has leathery waxy leaves and appears to be less appealing to slugs. No susceptibility or resistance to diseases or other pests has been observed.

I claim:

1. A new and distinct hybrid *Hosta* plant as herein shown and described.

* * * * *

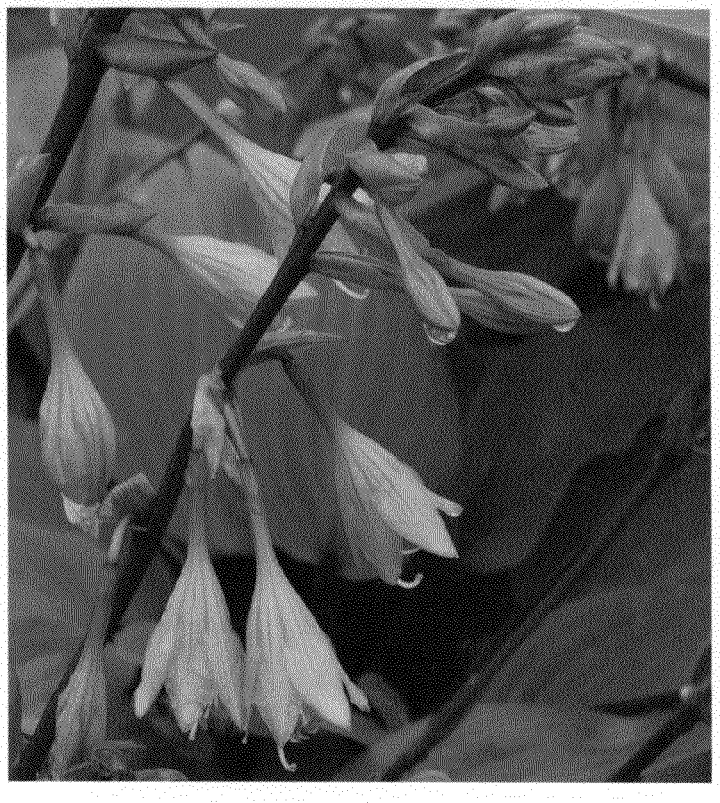

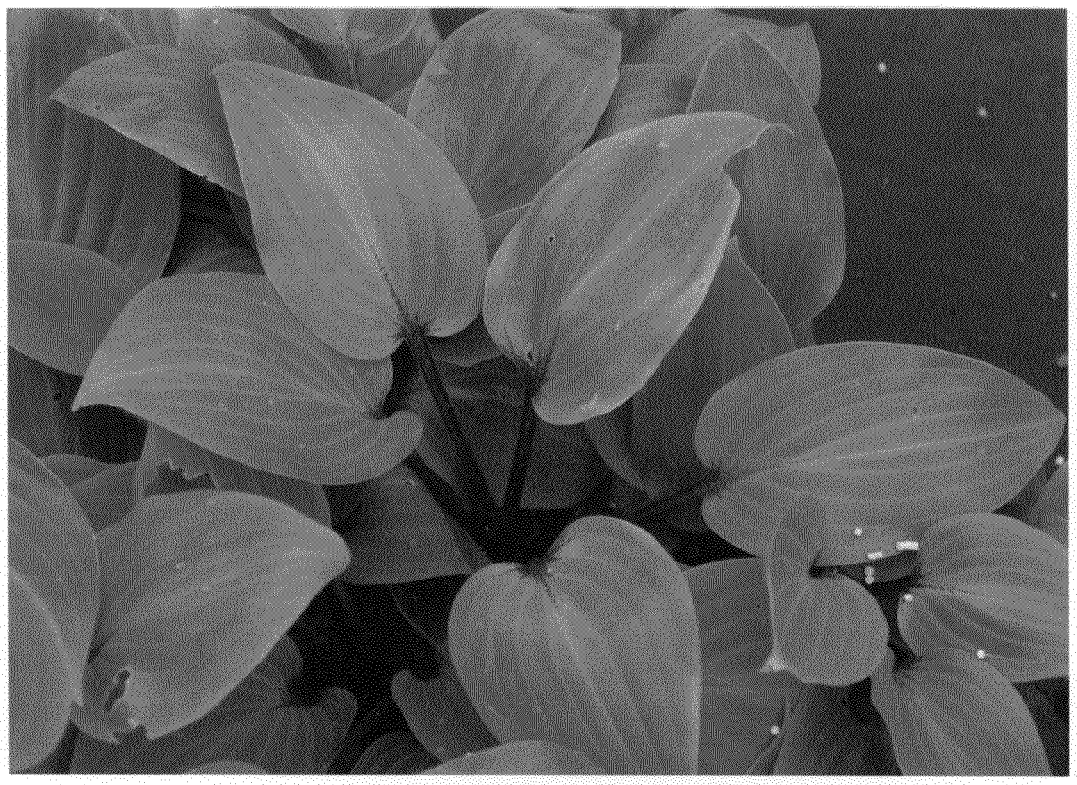
Figure 1 above
Figure 2 to right